(12) United States Patent
Magill

(10) Patent No.: US 6,774,643 B2
(45) Date of Patent: Aug. 10, 2004

(54) NON-BRIDGED SINGLE ELECTRODE IMPEDANCE MEASUREMENT SYSTEM FOR DETERMINING A CONDITION OF A DIELECTRIC ACCORDING TO IMPEDANCE RELATED CHANGES OVER A RANGE OF FREQUENCIES

(75) Inventor: Richard W. Magill, Broomfield, CO (US)

(73) Assignee: Signature Control Systems, Denver, CO (US)

( * ) Notice: Subject to any disclaimer, the term of this patent is extended or adjusted under 35 U.S.C. 154(b) by 109 days.

(21) Appl. No.: 10/102,614

(22) Filed: Mar. 19, 2002

(65) Prior Publication Data

US 2002/0135385 A1 Sep. 26, 2002

Related U.S. Application Data

(60) Provisional application No. 60/278,034, filed on Mar. 21, 2001.

(51) Int. Cl.[7] .............................................. G01R 27/26
(52) U.S. Cl. ........................ 324/663; 324/607; 324/658
(58) Field of Search ................................ 324/601, 603, 324/639, 663, 642, 646, 638, 658, 607

(56) References Cited

U.S. PATENT DOCUMENTS

| | | | |
|---|---|---|---|
| 2,765,219 A | 10/1956 | Shawhan | 23/253 |
| 3,746,975 A | 7/1973 | Maltby | 324/65 |
| 3,753,092 A | 8/1973 | Ludlow et al. | 324/61 |
| 3,778,705 A | 12/1973 | Maltby | 324/61 |
| 3,781,672 A | 12/1973 | Maltby et al. | 324/61 |

(List continued on next page.)

FOREIGN PATENT DOCUMENTS

| | | | |
|---|---|---|---|
| EP | 0 540 103 B1 | 2/1996 | C08K/5/3415 |
| EP | 0 743 153 A1 | 11/1996 | B29C/35/02 |
| EP | 1 050 888 A1 | 11/2000 | H01B/1/20 |
| WO | WO 99/13346 | 3/1999 | G01R/27/04 |

OTHER PUBLICATIONS

Real Time, In–Situ Dielectric Monitoring of Advanced Composites Curing Processes, Final Report, Phase I, Sponsored by Defense Advanced Research Projects Agency, 1988.

Keller et al., "Computer Controlled Processing of Composites Utilizing Dielectric Signature Curves", SAMPE Journal, vol. 28, No., 5, Sept./Oct. 1992, pp 25–33.

Lockheed Signature Process Control for Composites Proposal, Jul. 1, 1993, pp. 1–12.

(List continued on next page.)

Primary Examiner—N. Le
Assistant Examiner—John Teresinski
(74) Attorney, Agent, or Firm—Sheridan Ross P.C.

(57) ABSTRACT

A method and system for analyzing the state of a dielectric material is disclosed. The dielectric material is determined to be in a state, S, by determining a similarity or dissimilarity between: (a) a first set of impedance values derived from excitation of a capacitor having the dielectric material disposed between electrodes for the capacitor, and (b) a second set of predetermined corresponding impedance values indicative of the state S. For each of a plurality of electrical frequencies, there are corresponding impedance values in the first and second sets. Each such impedance values is one of a conductance and a capacitance value for the dielectric material. Thus, within a time period sufficiently short so that the dielectric material is expected to remain in a same state throughout the time period, each of the electrical frequencies is used to excite the capacitor, and corresponding response impedance values are derived that provide an impedance "snap shot" of the dielectric material. Accordingly, a most likely state for the dielectric material is determined from a similarity or dissimilarity between the snap shot (i.e. the first set hereinabove), and the second of predetermined corresponding impedance values for the state.

18 Claims, 8 Drawing Sheets

U.S. PATENT DOCUMENTS

| | | | |
|---|---|---|---|
| 3,879,644 A | 4/1975 | Maltby | 317/246 |
| 3,985,712 A | 10/1976 | Garst | 260/75 M |
| 4,331,516 A | 5/1982 | Meighan | 204/2.1 |
| 4,338,163 A | 7/1982 | Rittenhouse | 204/2.1 |
| 4,344,142 A | 8/1982 | Diehr, II et al. | 364/473 |
| 4,373,092 A | 2/1983 | Zsolnay | 528/481 |
| 4,381,250 A | 4/1983 | Rittenhouse | 252/182.1 |
| 4,399,100 A | 8/1983 | Zsolnay et al. | 422/62 |
| 4,423,371 A | 12/1983 | Senturia et al. | 324/61 R |
| 4,433,286 A | 2/1984 | Capots et al. | 324/61 |
| 4,448,943 A | 5/1984 | Golba, Jr. et al. | 526/59 |
| 4,496,697 A | 1/1985 | Zsolnay et al. | 526/60 |
| 4,510,103 A | 4/1985 | Yamaguchi et al. | 264/40.2 |
| 4,510,436 A | 4/1985 | Raymond | 324/61 |
| 4,515,545 A | 5/1985 | Hinrichs et al. | 425/143 |
| 4,551,103 A | 11/1985 | Vitale | 434/225 |
| 4,551,807 A | 11/1985 | Hsich et al. | 364/473 |
| 4,676,101 A | 6/1987 | Baughman | 73/304 |
| 4,723,908 A | 2/1988 | Kranbuehl | 432/37 |
| 4,773,021 A | 9/1988 | Harris et al. | 364/476 |
| 4,777,431 A | 10/1988 | Day et al. | 324/61 |
| 4,868,769 A | 9/1989 | Persson | 364/550 |
| 4,881,025 A | 11/1989 | Gregory | 324/61 |
| 5,008,307 A | 4/1991 | Inomata | 523/220 |
| 5,032,525 A | 7/1991 | Lee et al. | 436/55 |
| 5,184,077 A | 2/1993 | Day et al. | 324/693 |
| 5,201,956 A | 4/1993 | Humphrey et al. | 118/716 |
| 5,207,956 A | 5/1993 | Kline et al. | 264/40.6 |
| 5,208,544 A | 5/1993 | McBreaty et al. | 324/687 |
| 5,219,498 A | 6/1993 | Keller et al. | 264/40.2 |
| 5,223,796 A | 6/1993 | Waldman et al. | 324/687 |
| 5,283,731 A | 2/1994 | Lalonde et al. | 364/401 |
| 5,317,252 A | 5/1994 | Kranbuehl | 324/71.7 |
| 5,453,689 A | 9/1995 | Goldfine et al. | 324/239 |
| 5,459,406 A | 10/1995 | Louge | 324/688 |
| 5,486,319 A | 1/1996 | Stone et al. | 264/406 |
| 5,521,515 A | 5/1996 | Campbell | 324/674 |
| 5,528,155 A | 6/1996 | King et al. | 324/713 |
| 5,569,591 A | 10/1996 | Kell et al. | 435/29 |
| 5,749,986 A | 5/1998 | Wyatt | 156/64 |
| 5,872,447 A | 2/1999 | Hager, III | 324/71.1 |
| 5,874,832 A | 2/1999 | Gabelich | 324/688 |
| 5,898,309 A | 4/1999 | Becker et al. | 324/689 |
| 5,961,913 A | 10/1999 | Haase | 264/326 |
| 5,996,006 A | 11/1999 | Speicher | 709/218 |
| 6,043,308 A | 3/2000 | Tanahashi et al. | 524/495 |
| 6,472,885 B1 * | 10/2002 | Green et al. | 324/638 |

OTHER PUBLICATIONS

Northrop Aircraft Division RTM System Proposal, Apr. 1, 1993, pp. 1–12.

Textron Aerostructures Autoclave Process Control Proposal, Feb. 12, 1993, pp. 1–11.

Buczek et al., "Considerations in the Dielectric Analysis of Composites", 40th Int'l SAMPE Symposium, May 8–11, 1995, pp. 696–710.

"Automatic, Computer Controlled Processing of Advanced Composites", Small Business Innovation Research Program, Project Summary, 1988.

Buczek et al., "Self–Directed Process Control System for Epoxy Matrix Composites", 40th Int'l SAMPE Symposium, May 8–11, 1995.

"Notification of Transmittal of the International Search Report or the Declaration" from the Patent Cooperation Treaty in International Patent Application No. PCT/US02/32480 filed Oct. 9, 2002.

U.S. patent application Ser. No. 10/267,197, Van Doren et al. filed Oct. 8, 2002.

U.S. patent application Ser. No. 09/815,342, Van Doren et al. filed Mar. 21, 2001.

"Automatic, Computer Controlled, Processing of Advanced Composites"; *Defense Small Business Innovation Research (SBIR)Program*; Apr. 7, 1988; 25 pgs.

Baumgartner et al.; "Computer Assisted Dielectric Cure Monitoring in Material Quality and Cure Process Control"; *SAMPE Journal*; Jul./Aug. 1983; pp. 6–16.

"Critical Point Control/Statistical Quality Control Software Module"; *Micromet Instruments*; 1993; 2 pgs.

Desanges; "Changes in the Electrical Properties of Natural Rubber/Carbon Black Compounds During Vulcaniation"; *Revue Generale du Caoutchouc*; Dec. 1957; 34(12); pp. 631–649.

"Dielectric Cure Testing on Polyester Bulk Molding Compound"; *Holometrix Micromet*; 2001; 3 pgs.; http://www.holometrix.com/holometrix/m materialtest.asp.

"Dielectric Sensors"; *NETZSCH*; Feb. 21, 2002; pgs.

"Eumetric System III Microdielectrometer. . ."; *Holometrix Micromet*; 2001; 5 pgs.

"ICAM–1000—In–mold Monitoring For SPC, SQC, and CPC (Critical Point Control) of Thermoset Molding Operations"; *Micromet Instruments, Inc.*; at least as early as Mar. 1990; 4 pgs.

"ICAM–1000 Industrial Cure Analysis & Monitoring System"; *Micromet Instruments, Inc.*; Aug. 1, 1991; 1 pg.

"ICAM–2000 Multi–Channel Cure Analyzer"; *Micromet Instruments*; 1993; 2pgs.

Johnson et al.; "Production Implementation of Fully Automated, Closed Loop cure Control for Advanced Composite Strucutres"; $34^{th}$ *International SAMPE Symposium*; May 8–11, 1989; pp. 373–384.

Khastgir; "A Comparative Study of Step Curing and Continuous Curing Methods"; *Rubber World*; Jan. 1994; pp. 28–31.

"MDE Series 10 Cure Monitor"; *Holometrix Micromet*; at least as early as Mar. 15, 2000; 2 pgs.

"Mono–Probe"*TYT–NAM–MON*; Oct. 27, 2000; 1 pg.

O'Conor et al.; "Update to the Jun. 1990 Confidential Descriptive Memorandum"; *Micromet Instrument Inc.*; Dec. 1, 1990; 17 pgs.

Persson; "A Novel Method of Measuring Cure—Dielectric Vulcametry"; *Plastics and Rubber Processing and Applications*; 1987; 7(2); pp. 11–125.

"Product Selection Grid"; *Holometrix Micromet*; 2001; 1 pg.; http://www.holometrix.com/holometrix/m prgrid.asp.

Rajeshwar; "AC Impedance Spectroscopy of Carbon Black–Rubber Composites"; *Deparment of Chemistry and Biochemistry at The University of Texas as Arlington*; Sep. 21–24, 1999; 13 pgs.

SmartTrac Advertisement, *Automotive News*; May 21, 2001; 1 pg.

"SmartTrac"; *Innovative Aftermarket Systems, Inc.*; 2001; 2 pgs. http://www.ias–inc.net/pages/products/smart.html.

"The Eumetric System III Microdielectrometer"; *Micromet Instruments, Inc.*; Sep. 1991; 4 pgs.

"Thermokinetics"; *NETZSCH*; ; Nov. 8, 2001; 2 pgs.

"Tools Mount Sensors"; *NETZSCH*; Feb. 21, 2002; 2 pgs.

"Vulcanization of Natural Rubber"; *NETZSCH*; Nov. 8, 2001; 2 pgs.

* cited by examiner

*Embodiment Use As Rubber Cure State Analyzer*

Alternative Flowchart
Use as Rubber Cure State Analyzer

NON-BRIDGED SINGLE ELECTRODE IMPEDANCE MEASUREMENT SYSTEM FOR DETERMINING A CONDITION OF A DIELECTRIC ACCORDING TO IMPEDANCE RELATED CHANGES OVER A RANGE OF FREQUENCIES

RELATED APPLICATION

This application claims priority from U.S. Provisional Patent Application No. 60/278,034 filed on Mar. 21, 2001. The entire disclosure of the provisional application is considered to be part of the disclosure of the accompanying application and is hereby incorporated by reference.

FIELD OF THE INVENTION

The present invention is directed to determining a state of a dielectric material by determining a similarity or dissimilarity between: (a) a derived set of impedance values obtained from signals output by a capacitor having the dielectric material therein, and (b) one or more predetermined sets of impedance values, each such set indicative of a possible state for the dielectric material. In particular, each of the derived and predetermined sets has impedance values for a common plurality of electrical frequencies used to excite the capacitor. Each of the sets is presumed to correspond to a time interval that is sufficiently short so that the dielectric material is expected to remain in substantially the same state during the time interval.

BACKGROUND OF THE INVENTION

In many circumstances the quality of material(s), and/or the evaluation of a process of manufacturing material(s) can be determined by the unique responses of the material(s) to electrical currents flowing therethrough. In particular, electrical impedances of such a material(s) may be used to identify changes and/or differences in the dielectric of the material(s). Thus, during a manufacturing process, the monitoring of dielectric changes of a manufactured item has been used to determine whether the manufacturing process is producing items having desired characteristics. For example, in U.S. Pat. No. 5,219,498 by Keller et al., composite materials having fibers impregnated with polymeric matrices are cured or thermoformed in a heating system. While the composite material is curing, capacitance and conductance samplings are taken, over an extended time, and the shape or geometric characteristics of the curve(s) generated by the samples (e.g., topographical features) are used to determine whether the curing process is progressing as expected, or whether appropriate modifications to the process need to be timely introduced for yielding a high quality product from the curing process. For example, a rule base is used to identify such geometric curve characteristics. In particular, the Keller patent attempts to identify geometric curve characteristics such as peaks, valleys, flats, rises and falls, and if identified, then those geometric characteristics are used to determine the state or condition of the dielectric material. Accordingly, complex pattern matching techniques can be required to identify such geometric curve characteristics. Additionally, sampling frequency adjustments can be required to detect such relative curve characteristics. For example, the time sale can be critical in the Keller patent since it is concerned with, e.g., rates of change and whether such changes are negative or positive, or changing between negative and positive. Thus, substantial time and/or computational resources can be expended in determining a similarity between actual and desired geometric curve characteristics.

In many contexts, however, it is desirable to determine the state of a dielectric material by directly comparing capacitive and/or conductive response values to corresponding reference capacitive and/or conductive values for one or more electrical frequencies. Moreover, it is desirable to determine state capacitive and conductance (i.e., impedance) information regarding a dielectric material in substantially real-time and/or with reduced computational capabilities. Furthermore, it is desirable to determine such state information without concern for timing adjustments needed for matching geometric characteristics determined over an extended time period. Thus, it would be desirable to have a simpler, more efficient and substantially non-time scale dependent system for using dielectric related values of a material to thereby determine a state or condition of the material, and in particular, for a material whose condition needs to be determined in substantially real-time.

SUMMARY OF THE INVENTION

The present invention is a method and system for identifying a condition or state of a dielectric material (such as an, item of manufacture, or substance) by analyzing a "signature" of impedance related values for the dielectric material, wherein the values are derived from impedances of a range of one or more electrical frequencies applied to the dielectric material, and subsequently the values are compared to one or more sets of reference values. For example, such dielectric materials may include vulcanizates, resins, lubricating fluids, water, medical solutes, pharmaceuticals, and bulk chemicals such as isocyanates, polyurethanes, formaldahydes, epoxies, and phenolics that may be evaluated with the present invention for thereby: (a) changing a production process, (b) determining a contaminant level of such a dielectric material, or (c) identifying that a desired characteristic exists in the dielectric material.

The present invention determines such an impedance signature as a collection of discrete conductivity and capacitance values for each of a plurality of frequencies, wherein each of the values is obtained substantially simultaneously from a dielectric material being analyzed. Accordingly, the resulting impedance signature is similar to a "barcode", in that, for each frequency applied to the dielectric material, at least one of a conductivity and a capacitance (i.e., impedance) related value is obtained. Accordingly, for determining a state or condition of the dielectric material, the barcode analogy for such impedance signatures may be even further strengthened by representing each of the impedance related values as a value on a common predetermined impedance scale. Moreover, the resulting aggregate collection of impedance related values are compared to one or more predetermined such impedance barcodes having corresponding conductivity/capacitance related values for the same frequencies, wherein each such predetermined impedance barcode includes or identifies impedance related values indicative of a corresponding possible condition or state of the dielectric material. Thus, an impedance barcode obtained from the dielectric material may be compared with one or more of the predetermined impedance barcodes for determining similarities and/or differences between the barcodes. Thus, instead of determining a condition of a dielectric material by identifying and comparing geometric characteristics (e.g., peaks, valleys, rises, falls, etc.) of a curve obtained from pairs of points (t, imp), where imp is an impedance value and t is a corresponding sampling time, the present invention compares, for each of one or more of electrical frequencies: (a) one or more corresponding values, v, related to actual impedance responses obtained from the dielectric material being assayed with (b) one or more corresponding predetermined or designated impedance values $V_r$ that serve as reference values. Note, that unless otherwise stated, the terms "predetermined impedance value" and "designated impedance value" will be used interchangeably. The meaning intended by both terms is the combination of their meanings; i.e., a predetermined or designated impedance value that serves as a reference value for comparing with a derived impedance value for the same frequency.

More generally, an apparatus embodying the present invention can be characterized as having the following components (1.1) through (1.5) following:

(1.1) a repository for storing, for each of one or more predetermined possible states for a dielectric material, a corresponding set of designated impedance related values for the dielectric material, wherein for each of a plurality of electrical frequencies, one of said designated impedance related values is provided in said corresponding set, such that said designated impedance related values of said set are collectively indicative of the predetermined possible state of the dielectric material;

(1.2) a capacitor having first and second spaced apart capacitor plates and a dielectric material therebetween;

(1.3) a signal generator and a load resistor electrically connected in series to said first capacitor plate for exciting said capacitor, wherein said signal generator, in combination with said load resistor provide, for each of said plurality of electrical frequencies, a corresponding current at the frequency to said capacitor; wherein each of said corresponding currents is provided to said capacitor within a time interval that is sufficiently short so that the dielectric material is expected to remain in a same one of said predetermined possible states during said time interval;

(1.4) amplification and digitization components for: (a) receiving, for said electrical frequencies input to said capacitor, responsive signals from said capacitor, each said responsive signal indicative of an impedance of the dielectric material, and (b) amplifying and digitizing said responsive signals, thereby obtaining a plurality of derived impedance related values, wherein there is at least one of said derived impedance related values for each of said electrical frequencies; and (1.5) one or more analysis components for determining, for at least one of said predetermined possible states, one of a similarity and a dissimilarity between said derived impedance related values and said corresponding set of designated impedance values.

Moreover, it is an aspect of the present invention to perform the following steps:

(2.1) for each of one or more possible conditions, performing the following step (a):
 (a) establishing, for the possible condition, a corresponding set of designated impedance related values, wherein for each of a plurality of electrical frequencies, one of said designated impedance related values is provided, such that said designated impedance values of said set are collectively indicative of the possible condition of the dielectric material;

(2.2) providing, for each of said plurality of frequencies, an electrical current to a capacitor having the dielectric material disposed between first and second capacitor plates of said capacitor, thereby obtaining an electrical signal response from said capacitor indicative of an impedance response by said dielectric material to said frequency; wherein said signal responses are collectively identified as being received from said capacitor at a substantially identical time sufficiently short so that the dielectric material is expected to remain in a same one of said possible conditions during said time interval;

(2.3) obtaining, for each of said frequencies, a derived impedance measurement for said electrical signal response to said frequency, and thereby obtaining a plurality of said derived impedance measurements for said substantially identical time;

(2.4) determining, for at least one of said possible conditions, one of a similarity and a dissimilarity between: (a) said corresponding set for the at least one possible condition, and (b) said plurality of said derived impedance measurements;
 wherein a result from said step of determining is indicative of whether or not the dielectric material is in said at least one possible condition.

In at least one embodiment the present invention generates such impedance barcodes using a non-bridged single electrode that serves as a capacitor plate, and wherein the dielectric material to be analyzed is intermediate between this single electrode and some other planer or substantially planer conductive surface that can serve as the capacitor plate for pairing with the single electrode. Thus, with the present invention a capacitor can be created with the dielectric material to be analyzed provided between the two plates. In particular, the second plate of this capacitor may be a preexisting conductive surface that is used for the confining or forming of the dielectric material to be analyzed. For instance, the second plate of the capacitor for the present invention may be an electrically conductive portion of a tube, pipe or reservoir having a petrochemical therein (e.g., oil or hydraulic fluid) as the dielectric material to be assayed.

Regarding fluids such as petrochemicals, the present invention allows real time and/or continuous monitoring of impedance barcodes of the fluid for determining whether such barcodes vary sufficiently from one or more predetermined impedance barcodes so as to require activation of an alert signal and/or activation of an action for mitigating a change in the fluid indicated by the change in the impedance barcode. This embodiment of the present invention has significant advantages in, e.g., determining when to change oil or hydraulic fluids in engines or a vehicle. Typically such petrochemicals are changed according to a fixed maintenance schedule dependent upon some use related parameter such as mileage (for a vehicle), or the lapsed time since a last change. However, such criteria do not take into account the actual condition of the petrochemical. Thus, the present invention can be cost effectively provided within, e.g., motorized transports such as autos, buses, boats, trains, aircraft for more precisely indicating when such petrochemicals need to be changed.

Alternatively, the present invention may be used in determining the state-of-cure of a rubber product such as a gasket or seal by comparing the impedance barcodes of the cured rubber product sample to both an uncured reference sample and a 100% cured reference sample. Note that it is not uncommon for currently available prior art rubber cure analysis techniques to require a substantial time period, (e.g., 2–4 hours) for completing such a state-of-cure analysis. However, with the present invention, such an analysis may be performed in less than 20 minutes, and more preferably less than 5 minutes. Accordingly, by utilizing the present invention, substantially immediate corrective action can be initiated when the curing process is not proceeding as desired. Thus, in a production environment, such articles as tires, seals, bushings and other elastomeric components, the costly production of defective articles may be substantially alleviated by use of the present invention.

Additionally, other embodiments of the present invention may be used in medical diagnosis and analysis for determining impurities and/or contaminants in various fluids such as blood or urea. For example, for patients requiring kidney dialysis to remove impurities from their blood, such dialysis procedures are typically performed on a regularly scheduled basis regardless of the actual level of impurities in the patient's blood. As a result, the fluctuation in impurities may be substantial between dialysis sessions. Accordingly, by attaching a portable embodiment of the present invention to the patient, a continuous determination of the accumulation of blood impurities may be monitored for determining when a next dialysis session is likely to be necessary.

Additionally, the present invention may be used for determining a duration of a dialysis session according to a near real time monitoring of the dialyzing fluid flowing both into and out of a dialysis equipment during a dialysis session. In particular, a first capacitor according to the present invention may be provided to obtain impedance barcodes of clean dialysis fluid prior to entering the dialysis equipment, and a second capacitor according to the present invention may be used to obtain impedance barcodes of dialysis fluid exiting the dialysis equipment. Thus, the impedance barcodes of the incoming clean dialysis fluid may be used as a dynamic reference for comparing against impedance barcodes of exiting dialysis fluid for thereby determining when blood impurities in the exiting fluid are sufficiently low that the dialysis session can be terminated. Note that since such blood impurities may appear as ionic and dipolar abnormalities within the dialysis fluid, the impedance barcode differences between the reference impedance barcodes from the clean dialysis fluid, and the impedance barcodes of the exiting dialysis fluid may be statistically correlated so that, e.g., when such a correlation reaches a predetermined value (e.g., 99.5%), the removal of blood impurities is deemed to be essentially complete, and the dialysis session can be terminated.

Moreover, various other embodiments of the present invention may be used to continuously and/or in near real time monitor dielectric materials whose quality or purity is related to ionic and dipolar characteristics. For example, the present invention may be utilized for monitoring ground water purity, the purity of food products, the purity of pharmaceutical products, and for quickly identifying various types of contaminants within mass produced dielectric materials.

Since a non-bridged single electrode is the only sensing element provided by the present invention (as opposed to the two or three electrodes used in prior art systems), there is a substantially greater degree of flexibility regarding the physical orientation and position of this single electrode sensor for monitoring impedance barcodes of a dielectric material in the various embodiments of the present invention. In particular, an embodiment of the present invention may be more easily retrofitted onto pipes, or tubing in difficult to access places than prior art impedance measuring systems.

It is an aspect of the present invention that to obtain the impedance barcodes, the present invention provides a complex current for passing from the electrode sensor, through the dielectric material being monitored, and subsequently to the grounded second capacitor plate. In particular, the complex current is produced by a load resistor ($R_L$) placed in series with the capacitor, wherein this current is subsequently provided by the electrode sensor to the dielectric material, and the second capacitor plate. Accordingly, a complex voltage is measured across the resistor with a high precision amplifier for obtaining the impedance barcode as will be described further hereinbelow. Subsequently, since a plurality of frequencies are applied to the electrode sensor, a plurality of discrete of conductivity and capacitance measurements may be obtained from the resulting complex voltage measured across the resistor. Moreover, in at least some embodiments of the present invention, there is no bridge circuit coupled to the capacitor. Accordingly, in these embodiments, such conductivity and capacitance values are relative conductivity and capacitance values (i.e., relative to some predetermined scale). Thus, this plurality of conductivity and capacitance values form a spectral response (i.e., an impedance barcode) for the dielectric material, and such a barcode can be compared with, e.g., a desired predetermined impedance barcode for thereby interfering that the dielectric material has a particular characteristic (desirable or undesirable).

It is a further aspect of the present invention that the predetermined one or more impedance barcodes (for comparing with impedance barcodes obtained from the dielectric material being monitored) are stored in a data storage unit accessible by and/or included in the present invention. In particular, such predetermined impedance barcodes may be retrieved and compared against impedance barcodes from the dielectric material being monitored, wherein the comparator may perform a statistical correlation between the two barcodes (e.g., a statistical correlation relating to a similarity or dissimilarity in the positions of the barcode values for the corresponding frequencies) for determining, e.g., a most likely state or condition of the dielectric material. Moreover, note that such a statistical comparison may be performed substantially faster and/or on less expensive devices than prior art curve shape pattern matching techniques. In various embodiments of the invention, the following statistical techniques may be used:

(3.1) analysis of standard deviation for performing the following steps with the derived and designated impedance values:
  (1) establish a data file for the designated impedance values that contains the expected response for a plurality of frequencies;
  (2) obtain a plurality of sample sets of derived impedance values, and determine if the derived values match the designated impedance values within some allowable range of standard deviation;
  (3) make a determination of the purity/contamination/cure level based on the comparison.

(3.2) analysis of mean square error for performing the following steps with the derived and designated impedance values:
  (1) establish a data file for the designated impedance values that contains the expected response for a plurality of frequencies;
  (2) obtain one or more sample sets of derived impedance values, and determine if the derived values match the designated values within same allowable range of mean square error;
  (3) make a determination of the purity/contamination/cure level based on the comparison.

(3.4) histogram analysis performing the following steps with the derived and designated impedance values:

(1) establish a data file containing histograms (distributions) of designated impedance values at a plurality of frequencies;
(2) obtain one or more sample sets of derived impedance value, and plot the values against the histogram to determine if the response is within a normal range;
(3) make a determination of the purity/contamination/cure level based on the comparison.
(3.5) analysis of correlation coefficients performing the following steps with the derived and designated impedance values:
(1) establish a data file containing the normal response of a material as designated impedance values, for a plurality of frequencies;
(2) obtain a sample of derived impedance values for the same frequencies;
(3) calculate the correlation coefficient ($R^2$) between the data sets;
(4) use the $R^2$ number to make a determination of purity/contamination/cure level.

In an alternative embodiment, instead of retrieving such a predetermined impedance barcode, a program element may be provided that has been trained to detect patterns of similarities and/or dissimilarities between such predetermined impedance barcode and the actual impedance barcode from the dielectric material being monitored. Note that such a trained program element may be, for example, an artificial neural network (ANN). Accordingly, the ANN (or other trainable component) may be trained using one or more sample sets of impedance related values (for predetermined electrical frequencies), wherein at least some of the sample sets are indicative of a corresponding predetermined condition or state of the dielectric material. Thus, during operation of the present invention, impedance values derived from the output of the capacitor may be input to the ANN for determining a most likely one of one or more conditions of the dielectric material. Additionally, an embodiment of the present invention may include an expert system having a rule base for identifying distinctive similarities and/or dissimilarities in the barcodes.

It is also an aspect of the present invention that in some embodiments, a predetermined impedance barcode for comparing with those impedance barcodes being monitored is such that this predetermined barcode may be for a particular undesirable characteristic of the dielectric material. Accordingly, the present invention may test for similarities between a current impedance barcode and such a predetermined undesirable barcode for thereby initiating corrective actions and/or generating alarm messages. Further, note that in one embodiment, data for both predetermined desirable and predetermined undesirable impedance barcodes may be used for training a learning program element so that such a program element may be able to recognize particular characteristics of the (near) real time impedance barcodes obtained from the monitoring process without a direct comparison with data from such predetermined impedance barcodes.

It is a further aspect of the present invention that an output from an impedance barcode identification component (e.g., an impedance barcode comparison component) for classifying or identifying an impedance barcode may be used for directly controlling a process that can change characteristics of the dielectric material being monitored. Thus, the present invention may provide feedback data for controlling such a process. For example, the feedback data may be provided to a process controller such as a process controller for a chemical production facility for monitoring a purity of a chemical being produced, or, e.g., for monitoring the contaminant levels of waste products being expelled into the environment.

To summarize, the present invention in various embodiments includes one or more of the following aspects:

(4.1) A system for analyzing the molecular constituents of various dielectric substances using a dielectric response therefrom wherein there is (are):

(4.1.1) A sensor that is a capacitor plate for a capacitor. Any other grounded conductive surface in proximity to the sensor may act as the other capacitor plate for the capacitor. The material under analysis must then be between (or pass between) these two capacitor plates. The material under analysis then becomes the dielectric in the capacitor. Therefore, a capacitor is formed by the material, the sensor, and the grounded secondary surface.

(4.1.2) A sensor excitation in the form of a low-level AC voltage that is applied to the sensor of (4.1.1). The frequency of the sensor excitation may be rapidly changed (in excess of 10 frequency changes per second), to produce a plurality of sensor responses in substantially real-time for one or more frequencies. The sensor response is dependent upon not only the applied one or more excitation frequencies, but more importantly, on the ionic and dipolar makeup of the material under analysis.

(4.1.3) An electrical circuit, including the formed capacitor comprising the sensor and the material under analysis that becomes a capacitive element in the circuit. It is an important aspect of the present invention that the electrical circuit is not a bridge network. Rather, current is driven to the grounded conductive surface through the material under analysis. This means that at least one embodiment of the present invention is a single electrode system, rather than a multiple electrode system (the latter being required in a bridge network). Note that the driven current becomes a complex current due to the fact that it passes through a complex impedance in the formed capacitor. The complex current is driven across a load resistor prior to the capacitor, creating a complex voltage having the necessary information to derive the capacitance and conductance responses. This complex voltage is then measured and amplified, and passed on to a computer analysis unit.

(4.1.4) One or more computer analysis units for receiving the complex voltage after it is captured and digitized with an analog to digital (A/D) converter. The digitized data is then analyzed by the computer analysis units, to produce both conductance and capacitance data for each of the previously mentioned one or more frequencies. Therefore, in substantially real-time, a "barcode" of capacitance/conductance values is created representative of the impedance response of the material over a wide range of excitation frequencies. The computer analysis unit also contains a database, that stores one or more normal or expected responses, for the material under analysis (i.e., it contains prestored "barcodes" that describe certain states of the material under analysis). The one or more computer analysis units then compare the prestored "barcodes" with the measured "barcode". Based on this comparison, the computer analysis units make a determination about the state of the material. This determination may be: a determination of a purity, a determination of a contamination level, a determination of a cure state (such as in a vulcanizate), or any other physical effect which causes an ionic or dipolar change in the material under analysis.

(4.1.5) Various embodiments of the present invention may provide:

(4.1.5.1) The display of the derived barcodes wherein the display occurs to a human observer, substantially instantanenously after the one or more electrical frequencies are applied to the dielectric material;

(4.1.5.2) A common predetermined scale which upon substantially all of the derived impedance measurements have corresponding values.

(4.1.5.3) Both a capacitance and a conductance measurement for each electrical frequency instance applied to the dielectric material being assayed.

(4.1.5.4) A statistical comparison technique that may be performed between the stored and measured "barcodes" of impedance responses, in order to make a determination regarding the state of the material under analysis. Moreover, the statistical comparison technique may include one or more of the following (a)–(d):

(a) determining mean square error in comparing the stored and measured impedance values, (b) performing histogram analysis in comparing the stored and measured impedance values;

(c) performing a calculation of correlation coefficient between the stored and measured impedance values; and (d) comparison of the stored and measured impedance values, with a certain standard deviation tolerance.

(4.1.5.5) A determination of at least one possible condition, wherein the condition is indicative of one of (a)–(c) following:

(a) a quality of a petrochemical in an engine;

(b) a cure state of a rubber compound;

(c) a characteristic of a bodily fluid.

(4.1.5.6) The dielectric material as one of a vulcanizate, a resin, a thermoset, a thermoplastic, an oil, water, a medical solute, a pharmaceutical, and a bulk chemical.

(4.1.5.7) A computer analysis unit(s) and comparison methodology that may contain a trainable component, such as an artificial neural network (ANN), wherein a trainable component (such as an ANN), is used to make determinations regarding the state of the material under analysis.

Other features and benefits of the present invention will become evident from the accompanying drawings and the detailed description hereinbelow.

DETAILED DESCRIPTION OF THE PREFERRED EMBODIMENT

Figure 1:
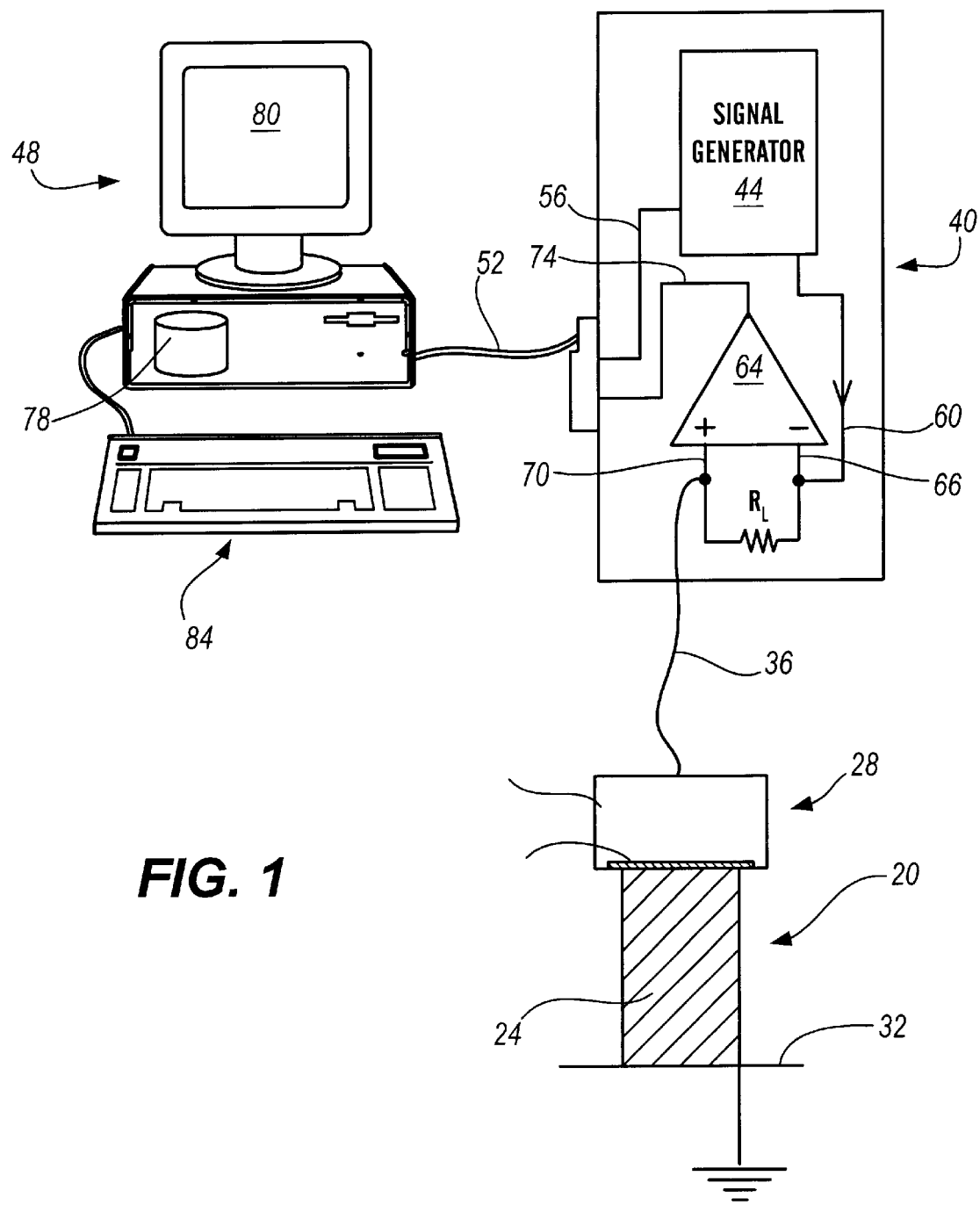
FIG. 1 shows an embodiment of the present invention for monitoring the state or condition of the dielectric material 24.

FIG. 1 shows a high level diagram of one embodiment of the present invention. The capacitor 20 provided by the present invention includes a dielectric material 24 to be assayed, an impedance sensor 28, and a grounded surface 32. The grounded surface 32 is electrically insulated from the impedance sensor 28 except for current induced to flow through the dielectric material 24. The impedance sensor 28 is electrically connected by cable 36 to a signal conditioning unit 40. The signal conditioning unit 40 includes a signal generator 44 for generating a current at various electrical frequencies. The signal conditioning unit 40 receives frequency specification input from the user's computational device 48 (e.g., a personal computer) via cable 52 and line 56. Upon receiving such input, the signal conditioning unit 40 outputs, via line 60, a current at a requested frequency to a load resistor $R_L$, and an amplifier 64 via negative amplifier input 66. Note that the load resistor $R_L$ is in series with the capacitor 20, wherein the current that flows through the capacitor 20 (and therefore also flows through the dielectric material 24 under analysis) also flows through the load resistor $R_L$, resulting in a voltage which can be measured by the amplifier 64.

When the current generated by the signal generator 44 is received by the capacitor 20, a voltage response from the capacitor is provided to the amplifier 64 via the cable 36 and the positive amplifier input 70. The amplifier 64 amplifies the voltage received from the capacitor 20 by, e.g., 100 times, and provides a corresponding amplified signal output to the user computational device 48 via line 74 and cable 52. Note that the user computational device 48 includes a data acquisition and storage device 78 for both storing electrical frequency input specifications that are to be provided to the signal generator 44, and storing digital data corresponding to voltage signals obtained from the capacitor 20. Thus, an analog to digital converter (not shown) is also included in the present invention.

Figure 2:
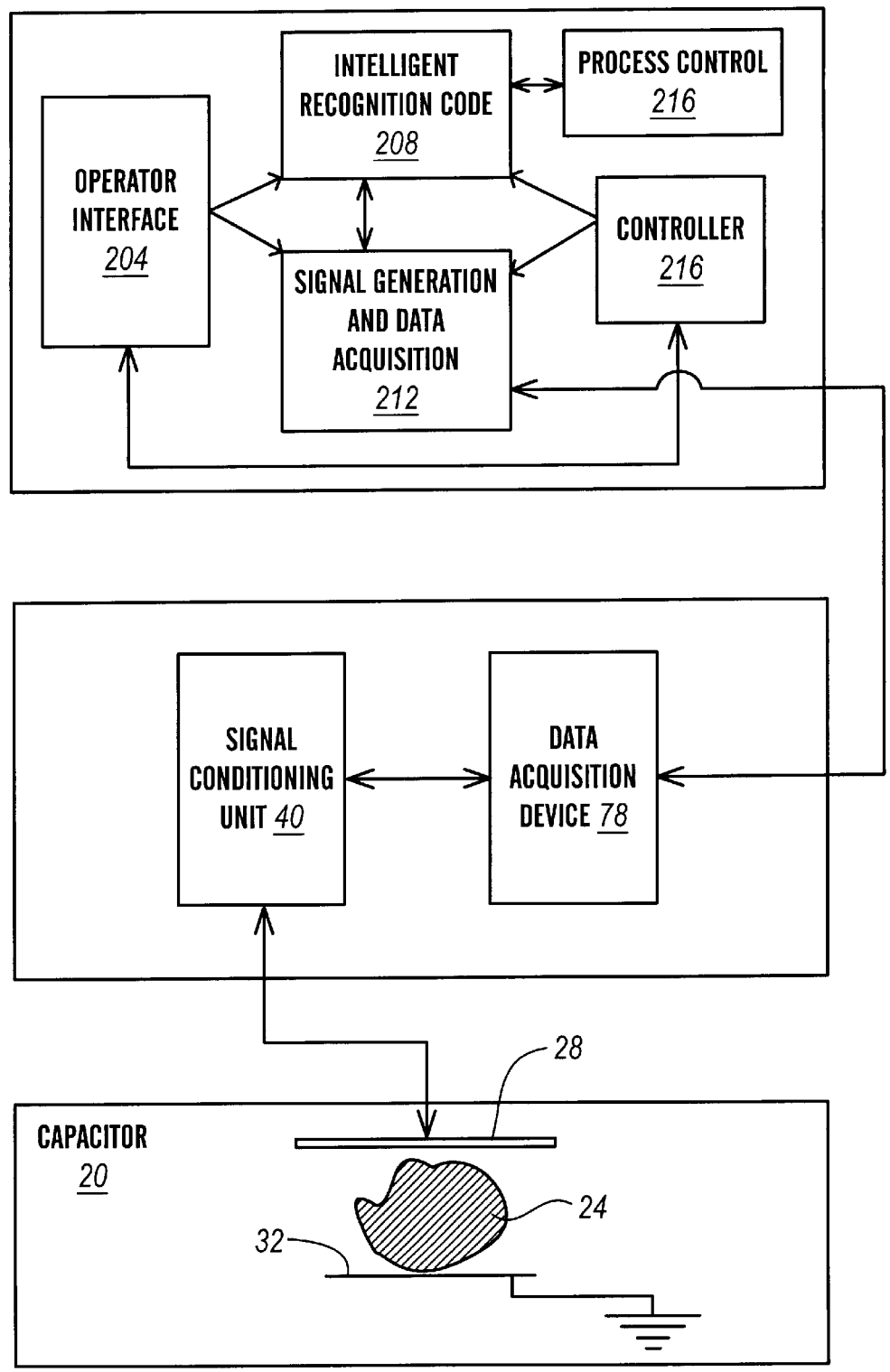
FIG. 2 shows a block diagram illustrating the major components of the embodiment of the present invention of FIG. 1.

Referring to FIGS. 1 and 2, note that the user computational device 48 preferably includes at least a display 80 and at least one user input device 84 such as a keyboard.

The operator interface 204 (FIG. 2) residing at the user computational device 48 communicates with an intelligent code recognition module 208, with signal generation and data acquisition modules 212 and a controller 214. The signal generation and data acquisition modules 212 interface with the data acquisition device 78 for storing therein and retrieving therefrom both impedance data derived from signals obtained from the capacitor 20, and predetermined corresponding impedance data collections for comparing with such derived impedance data. Note that it is an important aspect of the present invention that each data collection (derived or predetermined) include a representation of a plurality of (frequency, impedance value) pairs for each electrical frequency provided to the capacitor 20, wherein the derived impedance values are obtained from the capacitor 20 within a sufficiently short enough time interval in comparison to changes in the dielectric material 24 so that these derived impedance values can be viewed collectively as a "snap shot" of the impedance response of the dielectric material 24 at each of a plurality of electrical frequencies (e.g., such a time interval is no more than half an expected elapsed time for the dielectric material to transition into or out of any of the predetermined conditions for the dielectric material, wherein such predetermined conditions each have a corresponding predetermined (or designated) impedance data collection. Further note that the snap shot time interval is preferably substantially less half of the above described elapsed time, e.g., for dielectric materials cited herein). Moreover, each such collection of impedance values can be considered as a "signature" for the condition of the dielectric material 24, wherein each of the impedance values is one of a conductivity value and a capacitance value. Further note that, in one embodiment, there may be a predetermined numerical scale, wherein each of the impedance values is (or corresponds to) a numerical value on this predetermined scale. Also note that the values of the predetermined scale may be relative to one another independently of their corresponding frequency. Thus, for each derived impedance data set obtained from the dielectric material 24, the impedance values thereof can be considered as a discrete set of values for identifying a state or condition of the dielectric material 24. Accordingly, this set of discrete values is referred to herein as a "barcode".

Similarly, the signal generation and data acquisition modules 212 also provide the program elements (not shown) for storing and retrieving at least one predetermined impedance data set in/from the data acquisition device 78.

The intelligent code recognition module 208 includes program elements (not shown) for comparing a derived impedance data set with a predetermined or designated impedance data set for determining whether the two impedance data sets are sufficiently similar so that the condition or state information associated with the predetermined impedance data set can be inferred to exist in the dielectric material 24. In particular, the intelligent code recognition modules 208 may include program elements for one or more techniques for recognizing similarities between the predetermined impedance data set and the derived impedance data set. For example, a statistically based technique may be embodied therein such as a least squares, partial least squares technique or other regression techniques may be provided. Alternatively, other techniques for recognizing and/or distinguishing between patterns of numerical values may be provided, such as trained artificial neural networks.

A process control module 216 may be provided by the present invention, or in operative communication therewith, for controlling a process that substantially determines the condition or state of the dielectric material 24. For example, the process control 216 may include modules (a) for signaling when an oil or hydraulic fluid has changed characteristics sufficiently enough to require replacing, (b) for signaling when impurities and/or contaminants in various bodily fluids such as blood or urea sufficiently change impedance characteristics, (c) for signaling when impedance characteristics of a water supply changes sufficiently to imply that the water has a different level of a contaminant, (d) for identifying when an elastomeric, such as a rubber compound, has reached a given state of cure, or (e) for modifying substantially any process that alters the impedance of a dielectric material 24, and wherein measurements of the impedance (conductivity and/or capacitance) may be used to identify or infer a corresponding state or condition of the dielectric material.

The controller 214 controls the overall processing of the components of the present invention that reside on the user computational device 48. In particular, the controller 214 may coordinate activations and/or data flows between the operator interface 204, the intelligent code recognition module 208, and the signal generation and data acquisition modules 212.

Figure 3A:
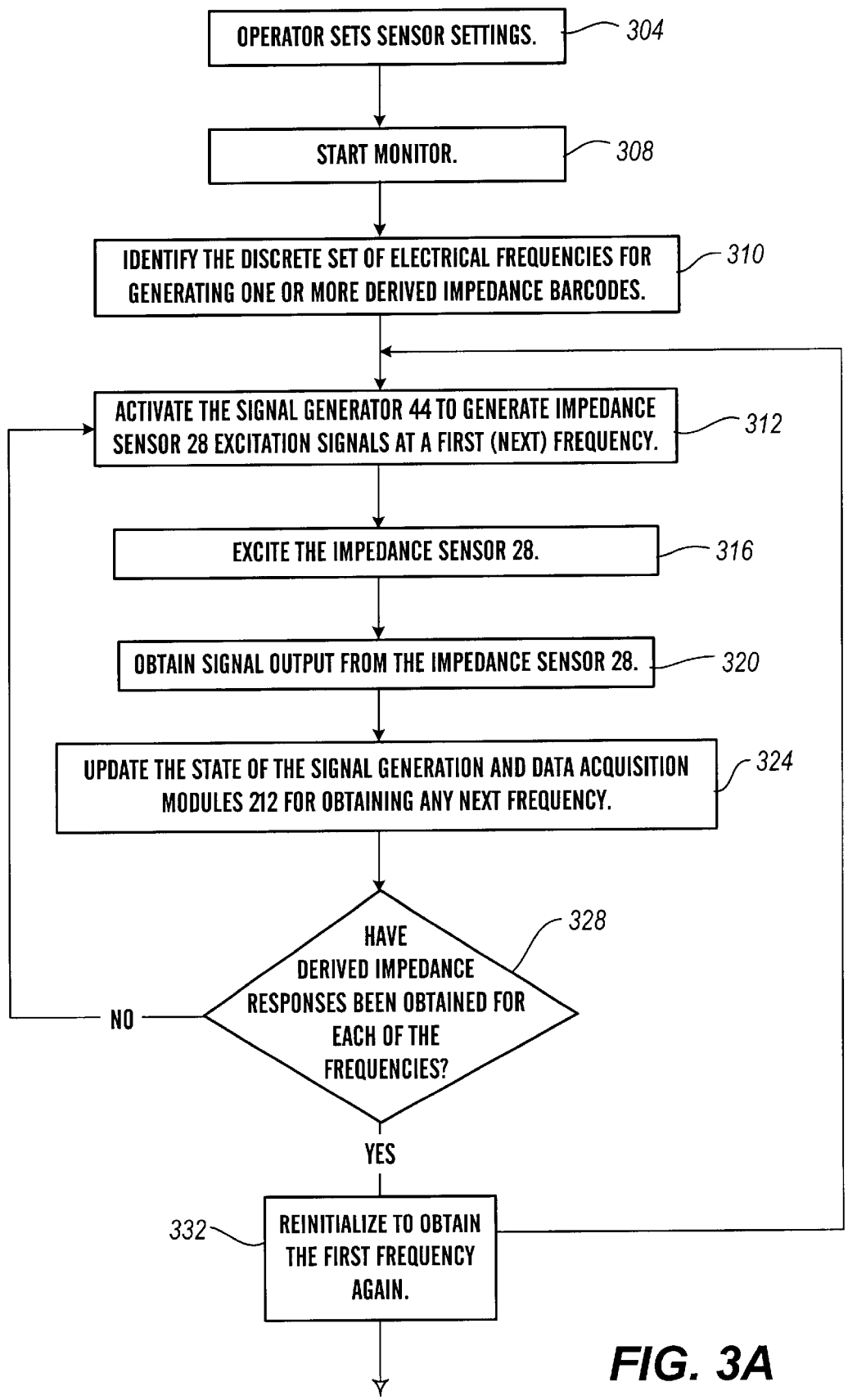
FIG. 3 is a flowchart describing the high level steps performed by the embodiment of FIGS. 1 and 2 when obtaining and analyzing impedance measurements.
Figure 3B:
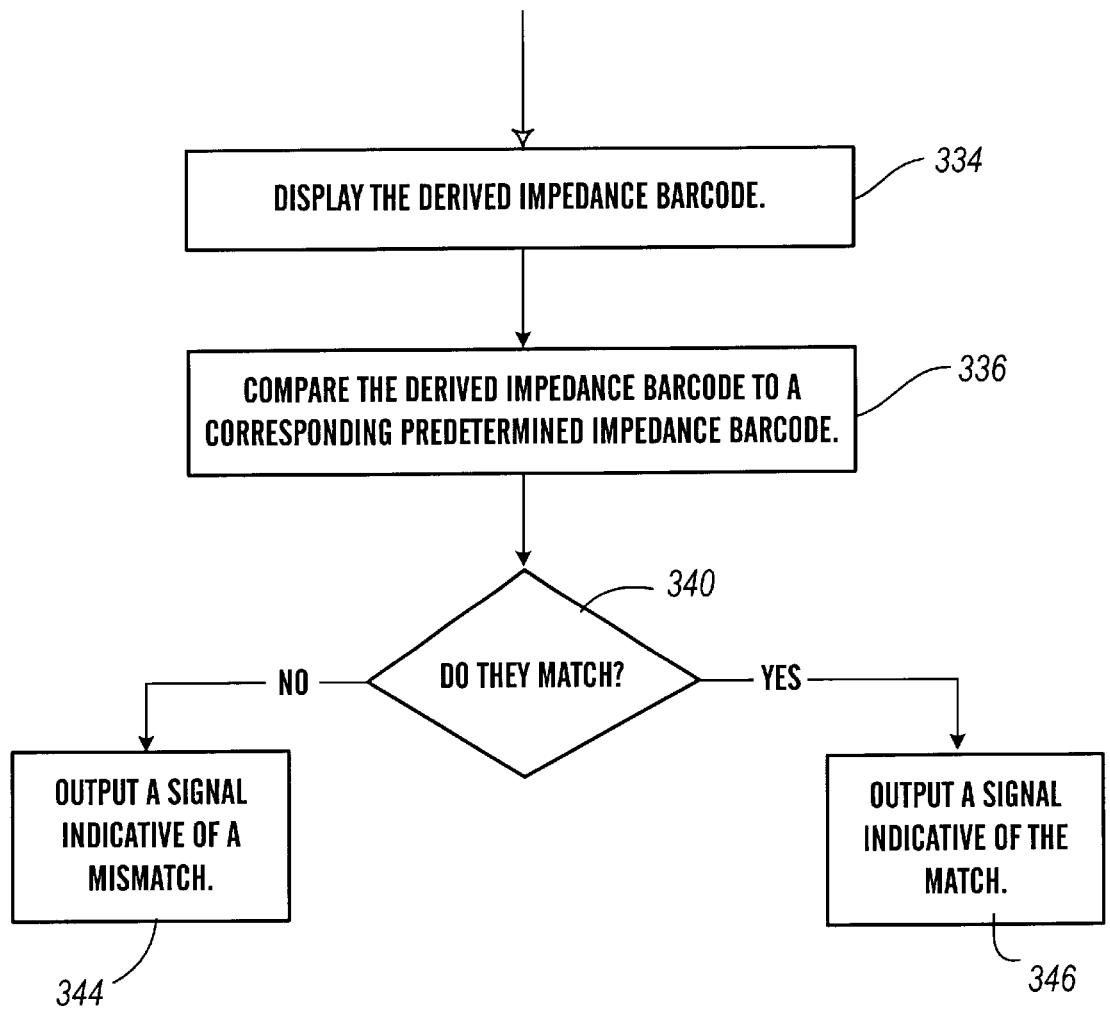

FIG. 3 provides a high level flowchart describing the steps performed by the present invention for monitoring the dielectric material 24 and potentially taking different processing control actions dependent upon a comparison of a derived impedance barcode (obtained from impedance data provided by capacitor 20), and a predetermined impedance barcode that is identified with a corresponding state or condition of the dielectric material 24. Moreover, the present flowchart is for an embodiment of the present invention wherein an operator or user provides input describing the predetermined impedance data and/or provides data identifying a state or condition of the dielectric material 24. However, one skilled in the art will readily understand that various modifications to the flowchart of FIG. 3 may be provided, such as the predetermined impedance data and the corresponding state or condition identification data may be provided from another source rather than a user. Proceeding to describe the steps of FIG. 3, in step 304, the user or operator inputs one or more of: (a) impedance sensor 28 information such as the electrical frequencies to be generated by the signal generator 44, (b) the predetermined impedance barcode, (c) information for indicating a state or condition of the dielectric material 24 when a derived impedance barcode sufficiently matches the predetermined impedance barcode, and (d) data identifying one or more barcode pattern matching modules (not shown) within the intelligent code recognition module 208 for performing the matching process between the predetermined impedance barcode and the derived impedance barcode. Subsequently, in step 308, the controller 214 is activated for controlling the processing performed within the user computational device 48. In step 312, the controller 214 instructs the signal generation and data acquisition modules 212 to identify and retrieve from the data acquisition device 78 a predetermined impedance barcode and its corresponding data representing a possible state or condition of the dielectric material 24. Additionally, the signal generation and data acquisition modules 212 are instructed to request that the data acquisition device 78 transmit to the signal conditioning unit 40 data indicating the electrical frequencies to be generated by the signal generator 44. Subsequently, in step 316, the signal conditioning unit 40 provides a first electrical frequency to the impedance sensor 28. In step 320, the signal conditioning unit 40, and more particularly, the amplifier 64, receives impedance signals from the capacitor 20 in response to the first input electrical frequency, wherein such signals are indicative of a conductivity or capacitance measurement of the dielectric material 24. Note that in order to receive signals indicative of conductance, the following steps are performed: the signal is (5.1) multiplied with the excitation such as by $(\sin(\omega t))$ as one skilled in the art will understand, and then (5.2) low pass filtered to provide an output proportional to the real portion of the complex voltage.

Alternatively, note that in order to receive signals indicative of capacitance, the following steps at performed: the signal is:
 (a) multiplied with the derivative of the excitation such as by (cos ωt) as one skilled in the art will understand, and then
 (b) low pass filtered to provide an output proportional to the imaginary portion of the complex voltage.

Accordingly, upon amplification of the impedance sensor 28 output signals by the amplifier 64, and subsequent conversion of the amplified signals to digital data by an analog to digital converter, the resulting digital impedance related values is transmitted to and stored in the data acquisition device 78. As mentioned hereinabove, the derived impedance data provided to the data acquisition device 78 is a relative value that may be compared with other similar relative values obtained from the impedance sensor 28 independently of the electrical input frequency. Moreover, note that such values are inherently relative, since there is no bridge circuit provided for the capacitor 20. Thus, the derived impedance data from the impedance sensor 28 may be somewhat unique to the capacitor 20.

Subsequently, in step 324, the signal generator 44 outputs a next frequency (assuming such exists) to the impedance sensor 28. Note that the output of any such next electrical frequency by the signal generator 44, may be in response to the signal generation and data acquisition modules 212 instructing the signal generator regarding the frequency to output and the duration of such output. Further note that the signal generation and data acquisition modules 212 may output such instructions to the signal generation module 44 after derived impedance data is received by the data acquisition device 78 in response to the previous electrical frequency signal for exciting the capacitor 20. Thus, in the present step (324) an index or pointer maintained in the signal generation and data acquisition modules 212 may be incremented to the presumed next frequency data used in constructing one or more commands to transmit to the signal generator 44. Accordingly, in step 328, a determination is made by the signal generation and data acquisition modules 212 as to whether there is indeed further frequency data for use in instructing and activating the signal generator 44. If all such frequency data has not been exhausted, then the steps 312–328 are again performed with the next frequency data that is identified by the incremented value obtained from step 324. Alternatively, if all such frequency data for determining their corresponding derived impedance barcodes has been transmitted and the results therefrom have been stored in the data acquisition device 78, then step 332 may be optionally encountered wherein the signal generation and data acquisition modules 212 are reinitialized for instructing the signal generator 44 to output the first frequency again after a desired elapsed time interval. Independently of any performance of step 332, in at least one embodiment, the step 334 is performed wherein the derived impedance barcode is displayed on the display 80. Note however that in some embodiments of the present invention, there may be no display 80 and no user input device 84. Further, the entire user computational device 48 may be provided on a single printed circuit board or on a single chip for automatically monitoring a condition or state of the dielectric material 24 without detailed output to a user of the derived impedance barcodes. In particular, the present invention may be embodied as a standalone substantially autonomous device placed in a substantially inaccessible location. Subsequently, in step 336, the intelligent code recognition modules 208 are activated for comparing the derived impedance barcode to at least one corresponding predetermined impedance barcode. Note that as mentioned hereinabove, the comparison may be performed by a statistical technique or some other pattern recognition technique where exact matching may not be necessary. For example, each value within the predetermined impedance barcode may have a range of values associated therewith and the comparison for determining whether there is an appropriate match may be determined by determining whether each of the values in the derived impedance barcode are within the range of the corresponding value in the predetermined impedance barcode. Accordingly, in step 340, a determination is made as to whether the derived impedance barcode sufficiently matches the at least one corresponding predetermined impedance barcode. If so, then step 350 is performed wherein a signal indicative of the derived and predetermined impedance barcodes matching is output. Alternatively, if it is determined in step 340 that there is a mismatch, then step 344 is performed wherein a signal indicative of a mismatch is output. Note that such output signals may be for the control of an actuator that is able to change the state or condition of the dielectric material 24. Alternatively, such output signals may provide alert signals to, e.g., a programmable logic controller for controlling a process that is able to modify the state or condition of the dielectric material 24. Moreover, it is within the scope of the present invention that at least one of the paths from the step 340 need not provide an output. For example, when an embodiment of the present invention monitors the impedance characteristics of oil within an engine, there may only be an output signal when the derived impedance barcode is sufficiently different from a preferred predetermined impedance barcode that is indicative of substantially clean oil. Thus, there would be no step 350, and step 344 would, e.g., provide a signal for activating an alert light indicating that the oil should be changed.

In other embodiments of the present invention, the corresponding predetermined impedance barcode used in step 336 may be for indicating an anomalous condition of the dielectric material 24 rather than a preferred condition. Accordingly, the step 350 may be used to output an alert signal indicating that the dielectric material 24 has diverged from an acceptable state or condition. Further, in other embodiments of the present invention, the step 336 may compare the derived impedance barcode with a plurality of corresponding predetermined impedance barcodes for determining the best match (if any). Accordingly, the present invention may be used to identify or diagnose a state or condition of the dielectric material 24.

Figure 4:
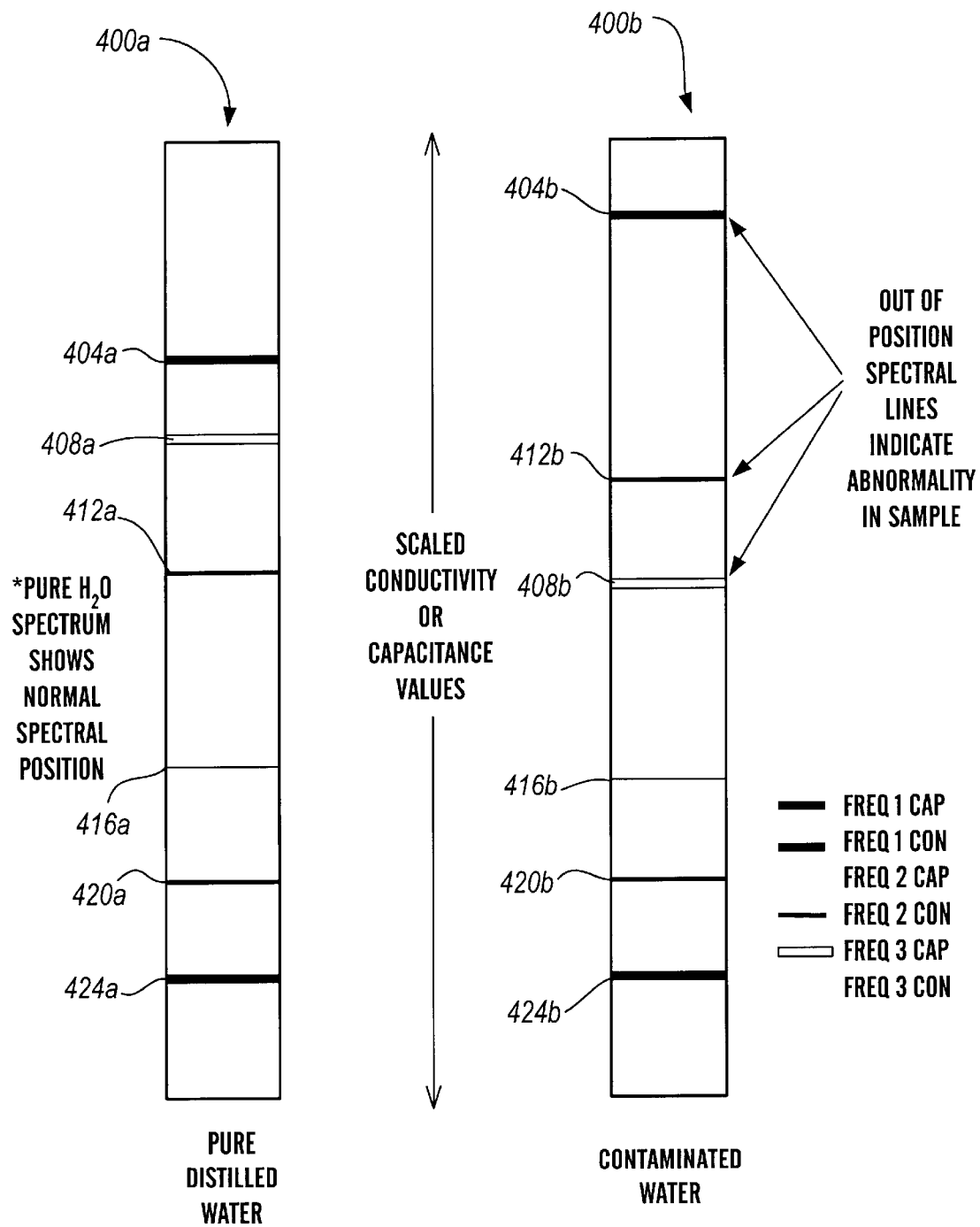
FIG. 4 shows: (a) a graph of an impedance barcode obtained from the dielectric material 24 illustrated in FIG. 1, and (b) a graph of the predetermined impedance barcode which the impedance barcode of (a) is compared.

FIG. 4 graphically illustrates one of the predetermined impedance barcodes (on the left), and an associated derived impedance barcode (on the right), wherein the predetermined barcode has horizontal lines 404a through 424a that are indicative of scaled impedance values at various frequencies for distilled water. In particular, the scaled value corresponding to line 404a corresponds to a conductivity value for a first frequency, the scaled value for line 408a corresponds to a capacitance value for the first frequency, the scaled value corresponding to 412a corresponds to a conductivity value for a second frequency, the scaled value 416a corresponds to a capacitance value for the second frequency, the scaled value corresponding to the line 420a corresponds to a conductivity value for a third frequency, and the scaled value corresponding to the line 424a corresponds to a capacitance value for the third frequency. Thus, when the predetermined impedance barcode 400a is compared with the in derived impedance barcode 400b, each of the impedance values corresponding to one of the lines 404*b* through 424*b* (of the derived impedance barcode) is indicative of a response from the dielectric material 24 at the same frequency and measures a same one of conductivity and capacitance as the same numerically identified line on the predetermined impedance barcode. Accordingly, note that the derived impedance barcode 400*b* may indicate that the water from which it was obtained is contaminated due to the difference in arrangement and position of the lines 404*b* through 412*b* in comparison to the corresponding lines 404*a* through 412*a*.

Figure 5:
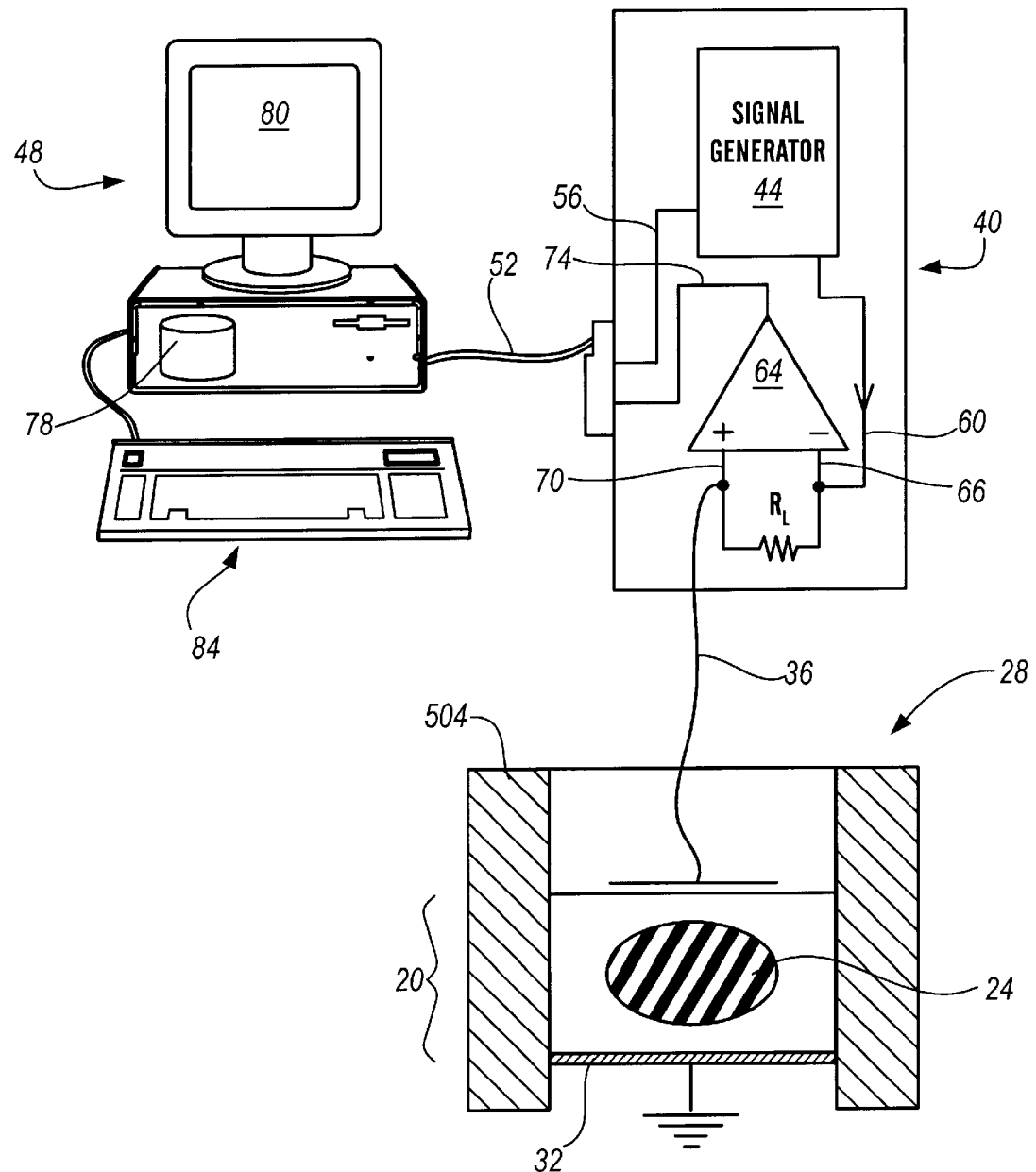
FIG. 5 shows an alternative embodiment of the components of the present invention for analyzing a cure state of a rubber compound.
Figure 6:
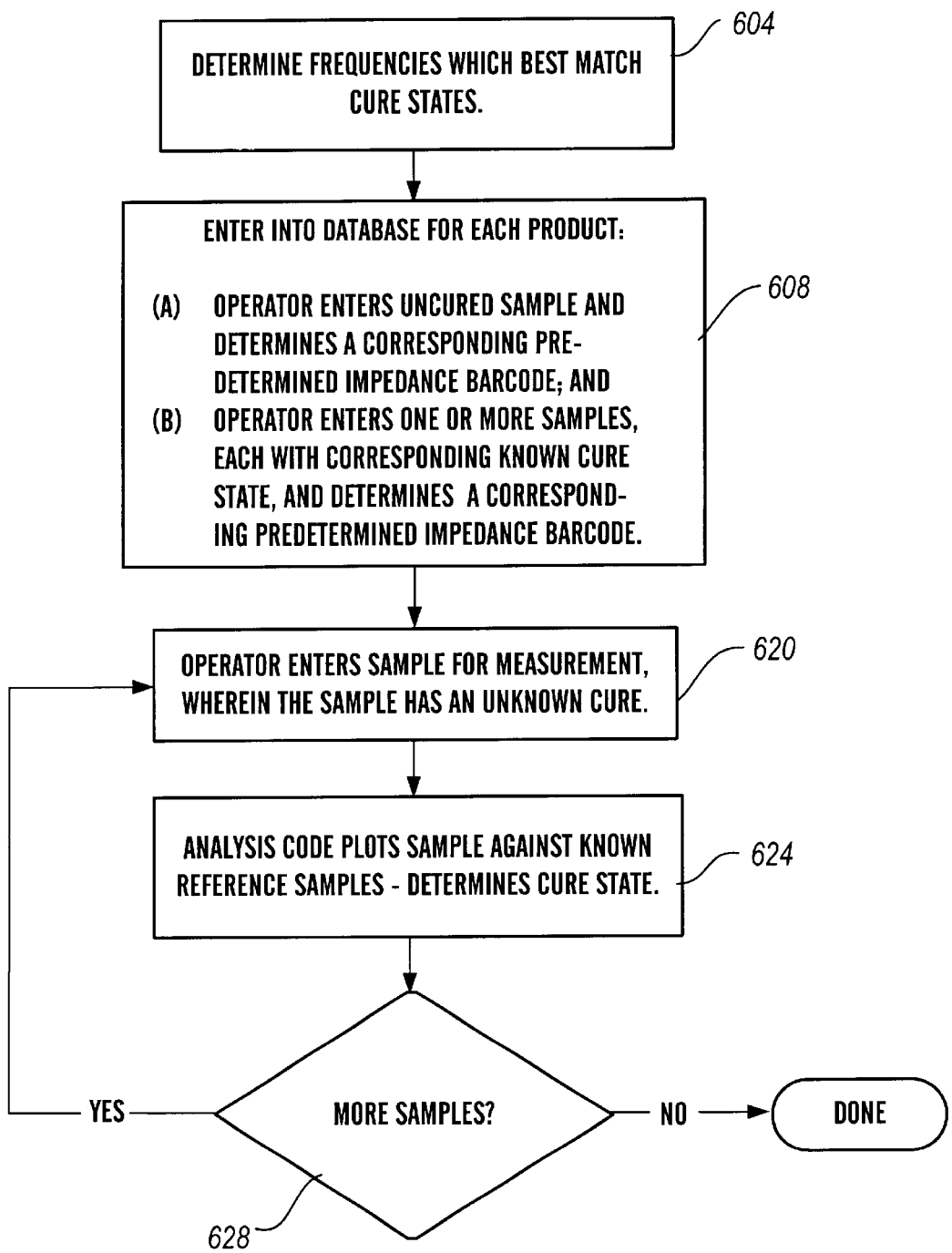
FIG. 6 provides a flowchart of steps performed by the rubber compound analysis embodiment of FIG. 5.

FIG. 6 illustrates an alternative embodiment of the present invention for use in analyzing and identifying a cure state for rubber as the dielectric material 24. Accordingly, the configuration of this figure is substantially identical to that of FIG. 1 with the exception that the capacitor 20 is integral with an outer housing having a heating element therein for heating the rubber sample 24 during curing. Thus, the present invention compares a derived impedance signature from the rubber sample 24 with a predetermined impedance signature for each of one or more rubber cure states for determining a best match and thereby inferring a corresponding cure state to the rubber sample 24. Note that the block diagram of FIG. 2 is also substantially applicable to the alternative embodiment of FIG. 5. However, at least in one embodiment of the process for analyzing the cure of rubber, the process control 216 may be unnecessary other than to alert an operator and/or a deactivation mechanism for reducing or terminating the heat applied to the rubber sample 24 by the outer housing 504. FIG. 6 illustrates a flowchart for the steps to be performed when determining the cure state of a rubber sample 24 according to the embodiment of the present invention illustrated in FIG. 5. Accordingly, in step 604, a determination is made as to the electrical frequencies for obtaining the corresponding conductivity and capacitance values for the embodiment of the invention in FIG. 5 wherein the resulting predetermined impedance barcodes provide acceptable information for inferring various cure states of the rubber sample 24. Accordingly, there may be one or more predetermined impedance barcodes identified from the determined frequencies, wherein, e.g., there may be an impedance barcode for a substantially uncured state, a partially cured state, a substantially fully cured state, and/or one or more impedance barcodes indicative of various anomalous states such as poor compound mixing, excessive porosity, foreign substance contamination, or an over aged compound. Subsequently, once the frequencies have been determined, step 608 is performed wherein for each rubber product to be cured, an operator provides a plurality of rubber samples 24, each having a known state of cure, within the capacitor 20 of the outer housing 504, wherein there are rubber samples 24 in various states of cure. Thus, for each such rubber sample 24, an impedance barcode reading is taken and stored as what has been referred to herein as a predetermined impedance barcode. In particular, step 608 provides at least two such impedance barcodes: one of a substantially uncured sample, and one of a substantially cured sample. Following this, in step 620, an operator provides a sample of unknown cure to the capacitor 20 of FIG. 5. In step 624, a derived impedance barcode is obtained and an analysis is performed to determine which cure state for the rubber sample being analyzed is most likely. In particular, the predetermined impedance barcodes provided in the database 78 that corresponds to the rubber product being assayed is compared to the derived impedance barcode obtained. Accordingly, the predetermined impedance barcode to which the derived impedance barcode best matches is indicative of the cure state of the rubber sample 24. Subsequently, in step 628, a determination made as to whether there are additional rubber samples 28 to assay regarding their cure states. Thus, steps 620–628 are repeated for each additional sample. Alternatively, the procedure of FIG. 6 terminates when there are no further samples.

Figure 7:
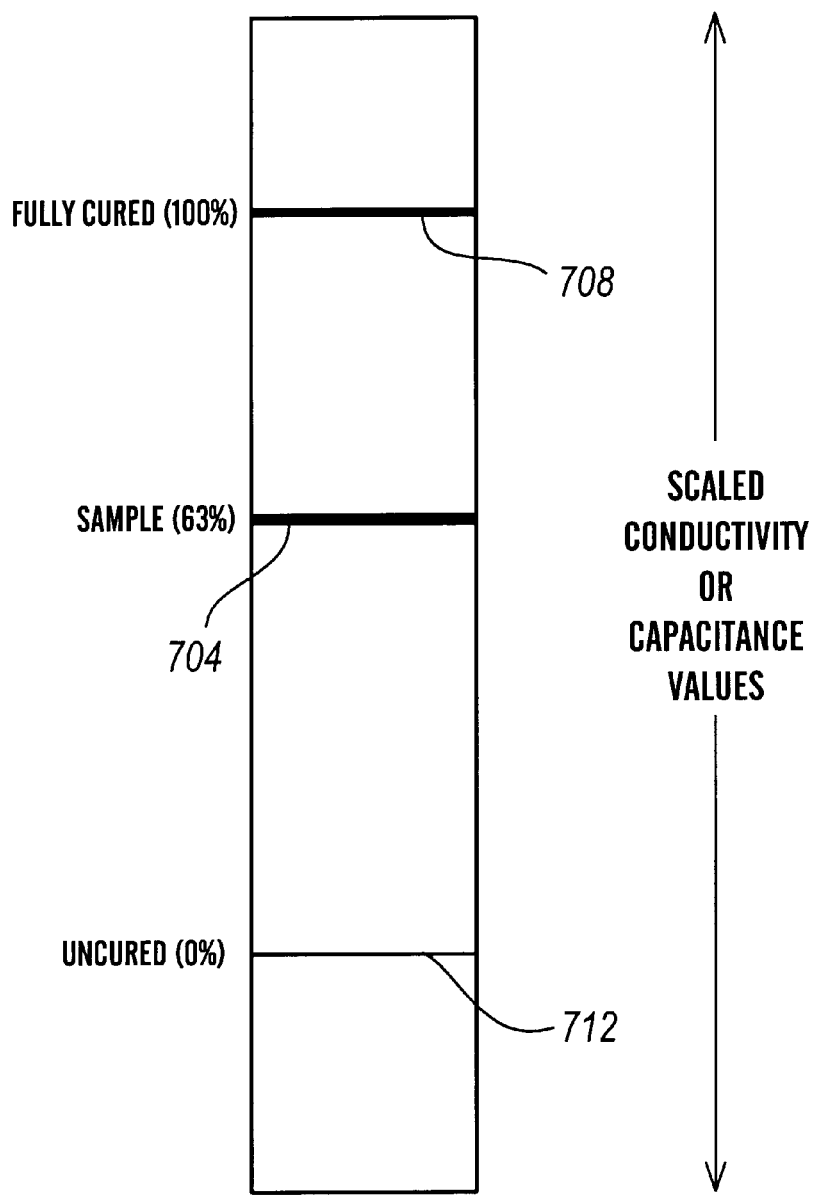
FIG. 7 graphically illustrates how an impedance measurement from the rubber sample 24 of FIG. 5 may be compared with the predetermined impedance values indicative of known rubber cure states such as a substantially uncured state and a substantially cured state.

FIG. 7 illustrates a comparison of a impedance value corresponding to line 704 on a scale for comparing it with a corresponding fully cured rubber sample identified by line 708, and an uncured impedance value corresponding to line 712. Note that the impedance values here may be either scaled conductivity values or scaled capacitance values. Also note that the impedance value corresponding to line 704 may be one of a plurality of such values within a derived impedance barcode provided by the embodiment of the present invention in FIGS. 5 and 6. Accordingly, an analysis may be performed by the present invention for determining the relative cure state of the rubber sample 24 according to how the one or more impedance values of the derived impedance barcode corresponds with the predetermined impedance values at corresponding frequencies, wherein the predetermined impedance values (for each corresponding frequency) includes: at least one value at a substantially uncured rubber state, and one value at a substantially fully cured rubber state. Accordingly, the present invention may perform an analysis over one or more frequencies for determining a most likely cure state for the rubber sample 24.

The foregoing discussion of the invention has been presented for purposes of illustration and description. Further, the description is not intended to limit the invention to the form disclosed herein. Consequently, variation and modification commensurate with the above teachings, and within the skill and knowledge of the relevant art, are within the scope of the present invention. The embodiments described hereinabove are further intended to explain the best mode presently known for practicing the invention, and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. A method for analyzing a dielectric material, comprising:

for each of one or more possible conditions, performing the following step (a):
(a) establishing, for the possible condition, a corresponding set of designated impedance related values, wherein for each of a plurality of electrical frequencies, one of said designated impedance related values is provided, such that said designated impedance values of said set are collectively indicative of the possible condition of the dielectric material;

providing, for each of said plurality of frequencies, an electrical current to a capacitor having the dielectric material disposed between first and second capacitor plates of said capacitor, thereby obtaining an electrical signal response from said capacitor indicative of an impedance response by said dielectric material to said frequency;

wherein said signal responses are collectively identified as being received from said capacitor at a substantially identical time sufficiently short so that the dielectric material is expected to remain in a same one of said possible conditions during said time interval;

obtaining, for each of said frequencies, a derived impedance measurement for said electrical signal response to said frequency, and thereby obtaining a plurality of said derived impedance measurements for said substantially identical time;

determining, for at least one of said possible conditions, one of a similarity and a dissimilarity between: (a) said corresponding set for the at least one possible condition, and (b) said plurality of said derived impedance measurements;

wherein a result from said step of determining is indicative of whether or not the dielectric material is in said at least one possible condition.

2. The method of claim 1, wherein said substantially identical time has a duration that is less than half an expected elapsed time for the dielectric material to transition into or out of any one of said possible conditions.

3. The method of claim 1, wherein substantially all of said derived impedance measurements are values of a common predetermined scale.

4. The method of claim 1, wherein there is no electrical bridge circuit including said first and second capacitor plates.

5. The method of claim 1, wherein said step of determining includes determining one of said similarity and said dissimilarity using at least two of said derived impedance measurements and at least two of said designated impedance related values of said corresponding set for said at least one possible condition.

6. The method of claim 1, wherein each said derived impedance measurement is one of a conductivity measurement and a capacitance value of the dielectric material.

7. The method of claim 1, wherein said step of providing includes generating a complex current for providing said complex current to said first capacitor plate, wherein said complex current is produced using a load resistor placed in series with said capacitor.

8. The method of claim 1, wherein said step of determining includes performing a statistical correlation technique for determining one of said similarity and said dissimilarity between said derived impedance measurements and said designated impedance related values of said corresponding set for said at least one possible condition.

9. The method of claim 8, wherein said statistical correlation technique includes one or more of:

a. determining a standard deviation of a value dependent upon differences between said derived impedance measurements and said designated impedance related values;

b. determining a mean square error between said derived impedance measurements and said designated impedance related values;

c. determining a comparison between histograms of derived and designated impedance values; and d. determining a correlation coefficient between said derived impedance measurements and said designated impedance related values of said corresponding set for said at least one possible condition.

10. The method of claim 1, wherein said at least one possible condition is indicative of one of:

a. a quality of a petrochemical in an engine;

b. a cure of a rubber compound; and c. a characteristic of a bodily fluid.

11. The method of claim 1, wherein the dielectric material is one of: a vulcanizate, a resin, a thermoset, a thermoplastic, an oil, water, a medical solute, a pharmaceutical, and a bulk chemical.

12. A method for analyzing a dielectric material, comprising:

for each of one or more predetermined conditions performing the following step:

establishing, for the predetermined condition, a corresponding set of impedance related values, wherein for each of a plurality of electrical frequencies, one of said corresponding impedance related values is provided, such that said corresponding values of said set are collectively indicative of the predetermined condition of the dielectric material;

providing, for each of said plurality of frequencies, an electrical current to a capacitor having the dielectric material disposed between first and second capacitor plates of said capacitor, thereby obtaining an electrical signal response from said capacitor indicative of an impedance response by said dielectric material to said frequency;

wherein said signal responses are collectively identified as being received from said capacitor at a substantially same time;

obtaining, for each of said frequencies, a derived impedance measurement for said electrical signal response to said frequency, and thereby obtaining a plurality of said derived impedance measurements for said substantially same time;

generating, substantially concurrently, an electrical current for each of said plurality of frequencies;

identifying a most likely one of said predetermined conditions for the dielectric material by determining one of a similarity and a dissimilarity between: (a) said corresponding set for the most likely predetermined condition, and (b) said plurality of said derived impedance measurements.

13. The method of claim 12, wherein said step of providing includes providing said current to an impedance sensor operatively connected to said first capacitor plate and only operatively connected to said second capacitor plate through said first capacitor.

14. The method of claim 12, wherein said step of identifying includes inputting said derived impedance measurements to a trainable component that has been trained using one or more sample sets of impedance related values for said plurality of frequencies, wherein at least some of said sample sets are indicative of one or more of the predetermined conditions.

15. The method of claim 12, wherein each of said derived impedance measurements is one of a conductivity and a capacitance value.

16. An apparatus for determining a state of a dielectric material, comprising:

a repository for storing, for each of one or more predetermined possible states for a dielectric material, a corresponding set of designated impedance related values for the dielectric material, wherein for each of a plurality of electrical frequencies, one of said designated impedance related values is provided in said corresponding set, such that said designated impedance related values of said set are collectively indicative of the predetermined possible state of the dielectric material;

a capacitor having first and second spaced apart capacitor plates and a dielectric material therebetween;

a signal generator and a load resistor electrically connected in series to said first capacitor plate for exciting said capacitor, wherein said signal generator, in combination with said load resistor provide, for each of said plurality of electrical frequencies, a corresponding current at the frequency to said capacitor;

wherein each of said corresponding currents is provided to said capacitor within a time interval that is sufficiently short so that the dielectric material is expected to remain in a same one of said predetermined possible states during said time interval;

amplification and digitization components for: (a) receiving, for said electrical frequencies input to said capacitor, responsive signals from said capacitor, each said responsive signal indicative of an impedance of the dielectric material, and (b) amplifying and converting said responsive signals, thereby obtaining a plurality of derived impedance related values, wherein there is at least one of said derived impedance related values for each of said electrical frequencies;

one or more analysis components for determining, for at least one of said predetermined possible states, one of a similarity and a dissimilarity between said derived impedance related values and said corresponding set of designated impedance values.

17. The apparatus of claim 16, wherein for each of said plurality of electrical frequencies, said corresponding current is provided to said capacitor through only one of said capacitor plates, and wherein said responsive signal for said corresponding current is also obtained from said only one capacitor plate.

18. The method of claim 16, wherein each said designated impedance related value is one of a conductivity measurement and a capacitance value for the dielectric material.

* * * * *